United States Patent [19]
DeVries et al.

[11] Patent Number: 4,489,090
[45] Date of Patent: Dec. 18, 1984

[54] DIBENZOCYCLOALKANAMIDO AND DIBENZOTHIOXANTHENYL BENZOIC ACIDS

[75] Inventors: Vern G. DeVries, Ridgewood, N.J.; Robert G. Shepherd, Selbyville, Del.

[73] Assignee: American Cyanamid Company, Stamford, Conn.

[21] Appl. No.: 492,097

[22] Filed: May 6, 1983

[51] Int. Cl.³ ............... A61K 31/22; A61K 31/38; C07C 103/733; C07D 335/12
[52] U.S. Cl. ................... 424/275; 424/309; 424/319; 549/26; 560/48; 562/457
[58] Field of Search ............ 542/415; 549/26; 560/48; 562/457; 424/275, 309, 319

[56] References Cited
U.S. PATENT DOCUMENTS
3,414,586 12/1968 Umemoto et al. ............ 549/26

FOREIGN PATENT DOCUMENTS
240866 6/1965 Austria .
44-13707 6/1969 Japan .

Primary Examiner—Richard L. Raymond
Attorney, Agent, or Firm—Edward A. Conroy, Jr.

[57] ABSTRACT

This disclosure describes novel dibenzocycloalkanamido-benzoic acids and esters. Also described are dibenzothioxanthenyl-benzoic acids and esters. These compounds are useful pharmaceutical agents for ameliorating atherosclerosis by inhibiting the formation and development of atherosclerotic lesions in the arterial walls of mammals.

9 Claims, No Drawings

DIBENZOCYCLOALKANAMIDO AND DIBENZOTHIOXANTHENYL BENZOIC ACIDS

BACKGROUND OF THE INVENTION

This invention relates to new organic compounds useful as pharmaceutical agents. The novel compounds of the present invention are antiatherosclerotic agents capable of ameliorating atherosclerosis by counteracting the formation or development of atheromatous lesions in the arterial wall of mammals. The invention also relates to the chemical synthesis of the novel compounds disclosed herein. In addition, the invention pertains to novel pharmaceutical compositions for the utilization of these compounds in the treatment of disease in mammals. Further, the invention contemplates methods for treating atherosclerosis in a manner designed to prevent, arrest, or reverse the course of the disease.

Atherosclerosis is a form of arteriosclerosis characterized by lipid accumulation in and thickening of the arterial walls of both medium- and large-sized arteries. Arterial walls are thereby weakened, and the elasticity and effective internal size of the artery is decreased. Artherosclerosis is the most common cause of coronary artery disease and is of great medical importance since the occlusion of medium- and large-sized arteries diminishes the supply of blood to vital organs such as the heart muscles and the brain. The sequelae to atherosclerosis include ischemic heart disease, heart failure, life-threatening arrythmias, senility, and stroke.

The fact that cholesterol is a major component of atherosclerotic lesions or plagues has been known for more than 100 years. Various researchers have studied the role of cholesterol in the lesion formation and development and also, more importantly, whether lesion formation can be prevented or lesion development arrested or reversed. Atheromatous lesions have now been shown [Adams, et al., Atherosclerosis, 13, 429 (1974)] to contain a greater quantity of esterified as opposed to unesterified cholesterol than the surrounding undiseased arterial wall. The intracellular esterification of cholesterol with fatty acids is catalyzed by the enzyme "Fatty acyl CoA: cholesterol acyl transferase" or ACAT and the accumulation and storage of cholesterol esters in the arterial wall is associated with increased levels of this enzyme [Hashimoto and Dayton, Atherosclerosis, 28, 447 (1977)]. In addition, cholesterol esters are removed from cells at a slower rate than unesterified cholesterol [Bonjers and Bjorkerud, Atherosclerosis, 15, 273 (1972) and 22, 379 (1975)]. Thus, inhibition of the ACAT enzyme would diminish the rate of cholesterol esterification, decrease the accumulation and storage of cholesterol esters in the arterial wall, and prevent or inhibit the formation and development of atheromatous lesions. The compounds of the present invention are very potent inhibitors of the ACAT enzyme. Thus, these compounds are useful for controlling and normalizing the cholesterol ester content of mammalian arterial walls. In contrast to the serum hypocholesterolemic agents which are well known in the art to merely lower cholesterol in the blood stream, the compounds of this invention decrease the accumulation and storage of cholesterol in the arterial walls of mammals. Further, the compounds of this invention inhibit the formation or development of atherosclerotic lesions in mammals. The exact mechanism by which these compounds exhibit this antiatherosclerotic activity is not known, and the invention should not be construed as limited to any particular mechanism of antiatherosclerotic action.

SUMMARY OF THE INVENTION

This invention relates to new organic compounds and more particularly is concerned with dibenzocycloalkanamido-benzoic acids and esters of the following structural formula:

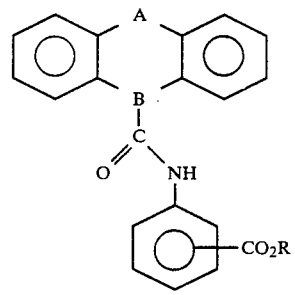

wherein A is selected from the group consisting of —$CH_2$—, —$CH_2CH_2$—, —CH=CH—, —O—, and —S—; B is selected from the group consisting of >$CHCH_2$— and >C=CH—; R is selected from the group consisting of hydrogen and $C_1$-$C_4$ alkyl; and the pharmaceutically-acceptable salts thereof.

Preferred embodiments of the invention relate to those compounds in which A is —$CH_2CH_2$—, —CH=CH—, and —S—. Of these, the most preferred are those compounds in which R is hydrogen and the alkali metal and alkaline earth metal salts thereof.

Representative specific embodiments include, for example, 4-(thioxanthene-9-acetamido)benzoic acid; 4-(5H-dibenzo[a,d]cycloheptene-$\Delta^{5,\alpha}$-acetamido)benzoic acid; and 4-(10,11-dihydro-5H-dibenzo[a,d]cycloheptene-$\Delta^{5,\alpha}$-acetamido)benzoic acid.

This invention also relates to a method of reducing the cholesterol content of the arterial walls of mammals which comprises administering to said mammal an effective amount of a compound as recited above.

This invention further relates to a method of inhibiting atherosclerotic lesion development in mammals which comprises administering to said mammal an effective amount of a compound as recited above.

This invention still further relates to a pharmaceutical composition which comprises an effective antiatherosclerotic amount of a compound as recited above in association with a pharmaceutically-acceptable carrier.

Finally, this invention relates to a process for preparing compounds as recited in claims 1, 2, 3, or 4, which comprises reacting a carbonyl compound of the formula:

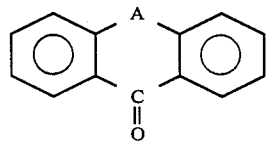

with a phosphonate ester of the formula:

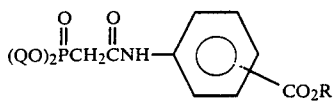

wherein A is defined as above and Q is selected from the group consisting of $C_1$–$C_4$ alkyl and phenyl; hydrolyzing the ester group —$CO_2R$ in the product to a carboxyl group; and converting the carboxy group to its alkali metal or alkaline earth metal salt.

DETAILED DESCRIPTION OF THE INVENTION

The esters of this invention are prepared by the reaction of appropriate ketones with a trialkyl ester of 4-(2-phosphonoacetamido)benzoic acid. Thus, dibenzosuberone is reacted with triethyl 4-(2-phosphonoacetamido)benzoate in hexamethylphosphortriamide in the presence of sodium hydride for 1–10 hours at 50°–100° C. After dilution of the reaction mixture with water, the product ethyl 4-[2-(10,11-dihydro-5H-dibenzo[a,d]cyclohepten-5-ylidene)acetamido]benzoate is isolated using an organic solvent such as dichloromethane. Similarly, the reaction of thioxanthone with triethyl 4-(2-phosphonoacetamido)benzoate in hexamethyl phosphortriamide in the presence of sodium hydride for 1–10 hours at 50°–100° C. affords ethyl 4-(thioxanthen-$\Delta^{9,\alpha}$-acetamido)benzoate. In the latter reaction, the product is purified by chromatography and ethyl 4-(thioxanthene-9-acetamido)benzoate is also isolated from the reaction mixture. Alternatively, esters such as this in which the bond between the tricyclic ring system and the carbon adjacent to the amido group is saturated, may be prepared by catalytic hydrogenation of the corresponding unsaturated esters.

The trialkyl esters of 4-(2-phosphonoacetamido)benzoic acid required for the above-described reaction are prepared as illustrated by the following example. Acylation of an alkyl ester of 4-aminobenzoic acid, such as ethyl 4-aminobenzoate, with bromoacetyl bromide yields ethyl 4-(bromoacetamido)benzoate. Reaction of this ester with triethylphosphite affords triethyl 4-(2-phosphonoacetamido)benzoate.

The carboxylic acids of this invention are prepared by alkaline hydrolysis of the corresponding esters. These carboxylic acids may be isolated as such by acidification or alternative isolated as their alkali metal or alkaline earth metal salts by evaporation.

The compounds of the present invention are generally obtained as crystalline solids having characteristic melting points and spectra. They are appreciably soluble in many organic solvents but are generally less soluble in water. Those compounds which are carboxylic acids may be converted to their alkali metal and alkaline earth salts by treatment with appropriate metal hydroxides, and these salts exhibit increased water solubility.

The preparation and properties of the compounds of this invention will be described in greater detail in conjunction with the specific examples shown below.

The compounds of the present invention were tested for their ability to inhibit the enzymatic esterification of cholesterol according to the following procedure:

Rat adrenals were homogenized in 0.2M monobasic potassium phosphate buffer, pH 7.4, and centrifuged at 1,000 times gravity for 15 minutes at 5° C. The supernatant, containing the microsomal fraction, served as the source of the cholesterol-esterifying enzyme, fatty acyl CoA:cholesterol acyl transferase (ACAT). A mixture comprising 50 parts of adrenal supernatant, 10 parts of albumin (BSA) (50 mg./ml.), 20 parts of oleoyl CoA ($^{14}$C-0.4 μCi), 3 parts of test compound, and 500 parts of buffer was pre-incubated at 37° C. for 10 minutes. After treatment with 20 parts of oleoyl CoA ($^{14}$C-0.4 μCi), the mixture was incubated at 37° C. for 10 minutes. A control mixture, omitting the test compound, was prepared and treated in the same manner. The lipids from the incubation mixture were extracted into an organic solvent and separated by thin-layer chromatography. The cholesterol ester fraction was counted in a scintillation counter. This procedure is a modification of that described by Hashimoto, et al., Life Scie., 12 (Part II), 1–12 (1973).

The results of this test on representative compounds of this invention appear in Table I. The final concentration of the test compound was 5.2 μg./ml., and effectiveness of the compound is expressed as percent inhibition of the ACAT enzyme as compared to control values.

TABLE I

| COMPOUND | % IN-HIBITION |
|---|---|
| Ethyl 4-[thioxanthene-9-acetamido]benzoate | 9 |
| 4-[Thioxanthene-9-acetamido]benzoic acid | 37 |
| Ethyl 4(5H—dibenzo[a,d]cycloheptene-$\Delta^5$,α-acetamido)benzoate | 20 |
| 4-(5H—dibenzo[a,d]cycloheptene-$\Delta^5$,α-acetamido)benzoic acid | 47 |
| 4-(10,11-Dihydro-5H—dibenzo-[a,d]cycloheptene-$\Delta^5$,α-acetamido)benzoic acid | 51 |

When the compounds are employed for the above utility, they may be combined with one or more pharmaceutically-acceptable carriers, e.g., solvents, diluents, and the like, and may be administered in such forms as tablets, capsules, dispersible powders, granules, suspension containing, for example, from about 0.5% to 5% of suspending agent, syrups containing, for example, from about 10% to 50% of sugar, and elixirs containing, for example, from about 20% to 50% ethanol, and the like, or parenterally in the form of sterile injectable solutions or suspensions containing from about 0.5% to 5% suspending agent in isotonic medium. These pharmaceutical preparations may contain, for example, from about 0.5% up to about 90% of the active ingredient in combination with the carrier, more usually between 5% and 60% by weight.

The antiatherosclerotic effective dosage of active ingredient employed for the reduction of cholesterol ester content in the arterial walls of a mammal may vary depending on the particular compound employed, the mode of administration, and the severity of the condition being treated. In general, however, satisfactory results are obtained when the compounds of the invention are administered at a daily dosage of from about 2 milligrams to about 500 milligrams per kilogram of animal body weight, preferably given in divided doses two to four times a day, or in sustained release form. For most large mammals, the total daily dosage is from about 100 milligrams to about 5,000 milligrams, preferably from about 100 milligrams to 2,000 milligrams. Dosage forms suitable for internal use comprise from about 25 milligrams to 2,500 milligrams of the active compound in intimate admixture with a solid or liquid pharmaceutically-acceptable carrier. This dosage regimen may be adjusted to provide the optimal therapeutic response. For example, several divided doses may be administered daily, or the dose may be proportionally reduced as indicated by the exigencies of the therapeutic situation. A decided practical advantage is that these active compounds may be administered orally as well as by intravenous, intramuscular, or subcutaneous routes if necessary. Solid carriers include starch, lactose, and kaolin, while liquid carriers include sterile water, polyethylene glycols, and edible oils such as corn, peanut, and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, e.g., vitamin E, ascorbic acid, BHT, and BHA.

The preferred pharmaceutical compositions from the stand-point of ease of preparation and administration are solid compositions, particularly tablets nd hard-filled or liquid-filled capsules. Oral administration of Compound I is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

EXAMPLE 1

Ethyl 4-(5H-dibenzo[a,d]cycloheptene-$\Delta^{5,\alpha}$-acetamido) benzoate

A solution of 96 ml. of bromoacetyl bromide in 800 ml. of dichloromethane is added during one hour to a stirred solution of 165 g. of ethyl 4-aminobenzoate and 165 ml. of triethylamine in 1 liter of dichloromethane while the temperature is maintained at less than 0° C. by ice-acetone cooling. The solution is then stirred at room temperature for 20 hours and extracted with two 1 liter portions of water. The solution is dried over magnesium sulfate, then evaporated, and the residue is crystallized from 2 liters of toluene to yield 223 g. of ethyl 4-(bromoacetamido)benzoate.

A mixture of 146 g. of the above ester and 230 ml. of triethylphosphite in 800 ml. of toluene is stirred and heated at 105°–110° C. for 2 hours, then cooled, and evaporated at 50° C. The residue is evaporated from three 400 ml. portions of hexane and then triturated with 300 ml. of hexane, to yield 170 g. of 4-(2-phosphonoacetamido)benzoic acid, triethyl ester.

To a suspension of 2.4 g. of hexane-washed sodium hydride (50% in oil) in 70 ml. of dry hexamethylphosphortriamide under argon is added 6.86 g. of 4-(2-phosphonoacetamido)benzoic acid, triethyl ester. The mixture is stirred 15 minutes, then 2.1 g. of dibenzosuber-5-enone are added, and the mixture is heated at 65°–70° C. for 3 hours. The mixture is cooled to 5° C., cautiously diluted with 400 ml. of water, stirred for ½ hour at 15° C., and filtered. The solid is washed successively with water, ether, ethyl acetate, and dichloromethane. The dichloromethane wash is evaporated to dryness, and the solid is dissolved in 300 ml. of hot dichloromethane, filtered, and the filtrate is concentrated to 75 ml. The resulting solid is collected, washed with dichloromethane, then acetone, and dried at 60° C. in vacuo, giving 1.4 g. of the desired product, m.p. 224°–226° C.

EXAMPLE 2

4-(5H-Dibenzo[a,d]cycloheptene-$\Delta^{5,\alpha}$-acetamido) benzoic acid

A mixture of 2.1 g. of ethyl 4-(5H-dibenzo[a,d]cycloheptene-$\Delta^{5,\alpha}$-acetamido) benzoate, 300 mg. of sodium hydroxide, 8 ml. of water, and 250 ml. of ethanol is refluxed for 4 hours, cooled, diluted with 500 ml. of water, and acidified with concentrated hydrochloric acid. After cooling and stirring for 30 minutes, the solid is collected, washed with water, dried, dissolved in 50 ml. of acetone, and filtered. To the filtrate is added 75 ml. of acetonitrile. The solvent is partially evaporated, and the solid is collected by filtration to yield 1.5 g. of the desired product as a white solid, m.p. 248°–250° C.

EXAMPLE 3

Ethyl 4-[2-(10,11-dihydro-5H-dibenzo[a,d]cyclohepten-5-ylidene)acetamido]benzoate To a suspension of 3.6 g. of hexane-washed sodium hydride (50% in oil) in 30 ml. of dry hexamethylphosphortriamide, under argon, is added dropwise a solution of 8.58 g. of 4-(2-phosphonoacetamido)benzoic acid, triethyl ester in 75 ml. of hexamethylphosphortriamide. This mixture is stirred for 20 minutes, then 5.21 g. of dibenzosuberone are added. This mixture is heated at 80°–85° C. for 6 hours, then cooled to 5° C., diluted with 500 ml. of water, and stirred for 30 minutes at 5° C. The solid is collected, washed with water, and dissolved in ethyl acetate. The ethyl acetate solution is washed with water, dried over magnesium sulfate, and evaporated to yield an oil. This oil is dissolved in 100 ml. of dichloromethane:hexane (1:1) and purified by preparative high pressure liquid chromatography on silica gel, eluting with 12% ethyl acetate in hexane, giving 1.0 g. of the desired product, m.p. 178°–180° C.

EXAMPLE 4 p-(10,11-Dihydro-5H-dibenzo[a,d]cycloheptene-$\Delta^{5,\alpha}$-acetamido)benzoic acid A mixture of 2.3 g. of ethyl 4-[2-(10,11-dihydro-5H-dibenzo[a,d]cyclohepten-5-ylidene)acetamido]benzoate, 300 mg. of sodium hydroxide, 5 ml. of water, and 150 ml. of ethanol is refluxed for 3 hours, cooled, and stripped to dryness. The residue is dissolved in water and extracted with three 75 ml. portions of ethyl acetate. The aqueous solution is acidified with concentrated hydrochloric acid, cooled, and stirred for 30 minutes. The solid is collected, washed with water, dried and dissolved in a hot mixture of 100 ml. of acetonitrile and 200 ml. of acetone. The solution is filtered, and the filtrate is evaporated to 75 ml. and cooled, giving 1.2 g. of the desired product, m.p. 256°–258° C.

EXAMPLE 5

Ethyl 4-(thioxanthen-Δ$^{9,\alpha}$-acetamido)benzoate

A mixture of 165 g. of ethyl 4-aminobenzoate, 165 ml. of triethylamine, and 1 liter of dichloromethane is cooled to 10° C.; then a solution of 96 ml. of bromoacetyl bromide in 800 ml. of dichloromethane is added slowly, maintaining the reaction temperature at less than 10° C. The mixture is then stirred overnight at room temperature, washed with 3 liters of water, dried over magnesium sulfate, and evaporated to dryness. The solid is crystallized from 1.2 liters of hot toluene and on cooling yielded 194 g. of ethyl 4-(2-bromoacetamido)benzoate.

A mixture of 164 g. of the above ester, 258 ml. of triethylphosphite, and 897 ml. of toluene is placed in a preheated 110° C. bath for 10 minutes and then heated at 105° C. for 2 hours. The mixture is cooled, the solvent is evaporated at 50° C., and the residue is reevaporated from three 500 ml. portions of hexane, giving an oil. This oil is triturated with 800 ml. of hexane, giving 188 g. of 4-(2-phosphonoacetamido)benzoic acid, triethyl ester.

To a suspension of 3.36 g. of hexane-washed sodium hydride (50% in oil) in 110 ml. of dry hexamethylphosphortriamide is added 10.92 g. of 4-(2-phosphonoacetamido)benzoic acid, triethyl ester under argon. This mixture is stirred 25 minutes, then 4.25 g. of thioxanthone are added. This mixture is heated at 65°–75° C. for 6 hours, cooled to 5° C., diluted with water, and stirred at 15° C. for 30 minutes. The solid is collected, washed with water, ether, and dichloromethane. The organic extracts are combined, stripped to dryness, and the solid is dissolved in 200 ml. of hot acetonitrile and filtered. The filtrate is evaporated to dryness, giving a solid which is dissolved in a mixture of 25 ml. of dichloromethane and 25 ml. of hexane and purified by preparative high pressure liquid chromatography on a silica gel column, eluting with 10% ethyl acetate in hexane, giving 1.71 g. of the desired product as a yellow solid, m.p. 175°–177° C.

EXAMPLE 6 p-(Thioxanthene-Δ$^{9,\alpha}$-acetamido)benzoic acid

A mixture of 7.0 g. of ethyl 4-(thioxanthene-Δ$^{9,\alpha}$-acetamido)benzoate, 800 mg. of sodium hydroxide, 5 ml. of water, and 300 ml. of ethanol is refluxed for 4 hours, cooled, and the solid is collected. This solid is dissolved in methanol, acidified with dilute hydrochloric acid, diluted with water and stirred for 30 minutes. The solid is collected, washed with water, dried, and crystallized from tetrahydrofuran:hexane, giving 2.64 g. of the desired product, m.p. 265°–266° C. (dec.).

EXAMPLE 7

Ethyl 4-[(9-thioxanthenyl)acetamido]benzoate

A solution of 30 g. of ethyl 4-(thioxanthen-Δ$^{9,\alpha}$-acetamido)benzoate in 250 ml. of cyclohexane was treated with 1.6 g. of platinum oxide and shaken under 40 p.s.i. of hydrogen for about 6 hours. The mixture was filtered and the filtrate evaporated. The residue was crystallized from hexane, giving 1.2 g. (4%) of the desired product, m.p. 184°–186° C.

EXAMPLE 8

4-[(9-Thioxanthenyl)acetamido]benzoic acid

Alkaline hydrolysis of ethyl 4-[(9-thioxanthenyl)acetamido]benzoate in the manner of Example 6 afforded 41% of the desired product, m.p. 265°–266° C.

EXAMPLE 9

Ethyl 4-(10,11-dihydro-5H-dibenzo[a,d]cyclohepten-5-ylacetamido)benzoate

Catalytic hydrogenation of ethyl 4-[2-(10,11-dihydro-5H-dibenzo[a,d]cyclohepten-5-ylidene)acetamido]benzoate in the manner of Example 7 afforded 18% of the desired product, m.p. 178°–180° C.

EXAMPLE 10

4-(10,11-Dihydro-5H-dibenzo[a,d]cyclohepten-5-ylacetamido)benzoic acid

Alkaline hydrolysis of ethyl 4-(10,11-dihydro-5H-dibenzo[a,d]cyclohepten-5-ylacetamido)benzoate in the manner of Example 4 afforded 77% of the desired product, m.p. 248°–250° C.

No effort has been made to optimize the yields obtained in the aforementioned Examples.

We claim:

1. A compound of the formula:

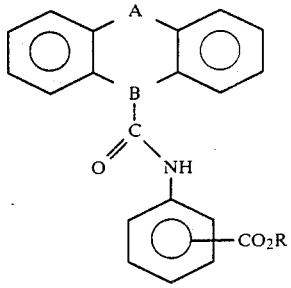

wherein A is selected from the group consisting of —CH$_2$CH$_2$—, —CH=CH—, and —S—; B is selected from the group consisting of >CHCH$_2$— and >C=CH—; R is selected from the group consisting of hydrogen and C$_1$–C$_4$ alkyl; and the pharmaceutically-acceptable salts thereof.

2. A compound as recited in claim 1 wherein R is hydrogen.

3. A compound as recited in claim 2 which is an alkali metal or alkaline earth metal salt.

4. The compound according to claim 1, 4-(thioxanthene-9-acetamido)benzoic acid.

5. The compound according to claim 1, 4-(5H-dibenzo[a,d]cycloheptene-Δ$^{5,\alpha}$-acetamido)benzoic acid.

6. The compound according to claim 1, 4-(10,11-dihydro-5H-dibenzo[a,d]cycloheptene-Δ$^{5,\alpha}$-acetamido)benzoic acid.

7. A method of reducing the cholesterol ester content of the arterial walls of a mammal in need of such treatment which comprises administering to said mammal an effective amount of a compound as recited in claim 1.

8. A method of inhibiting artherosclerotic lesion development in a mammal in need of such treatment which comprises administering to said mammal an effective amount of a compound as recited in claim 1.

9. A pharmaceutical composition which comprises an effective antiatherosclerotic amount of a compound as recited in claim 1 in association with a pharmaceutically-acceptable carrier.

* * * * *